United States Patent [19]

Pestes

[11] Patent Number: 4,468,914
[45] Date of Patent: Sep. 4, 1984

[54] APPARATUS FOR FILLING PETRI DISHES
[75] Inventor: Arlin N. Pestes, Gresham, Oreg.
[73] Assignee: Biomed Design, Inc., Vancouver, Wash.
[21] Appl. No.: 216,072
[22] Filed: Dec. 15, 1980
[51] Int. Cl.³ ............................. B65B 57/06; B65B 43/40
[52] U.S. Cl. ....................................... 53/505; 53/381 A; 141/102; 251/7
[58] Field of Search ................. 53/381 A, 282, 281, 53/67, 55, 505, 56, 474, 240, 250, 315, 506; 141/102, 159, 186, 156, 154, 350; 251/7, 9, 6

[56] References Cited
U.S. PATENT DOCUMENTS

| | | | |
|---|---|---|---|
| 2,353,200 | 7/1944 | Sundell | 53/313 X |
| 2,752,083 | 6/1956 | Ullman et al. | 141/102 |
| 2,817,461 | 12/1957 | Gilberty | 53/281 X |
| 2,978,854 | 4/1961 | Fairest | 53/250 X |
| 3,050,915 | 8/1962 | Silverstolpe | 53/381 A |
| 3,129,544 | 4/1964 | Klapes et al. | 53/240 X |
| 3,408,789 | 11/1968 | Reddick | 53/315 |
| 3,411,534 | 11/1968 | Rose | 251/9 X |
| 3,450,152 | 6/1969 | Ouellette | 251/9 X |
| 3,513,621 | 5/1970 | Chamberlin | 53/381 A |
| 3,704,568 | 12/1972 | Duhring et al. | 53/381 A |
| 3,719,023 | 3/1973 | Richardson | 53/381 A |
| 3,887,110 | 6/1975 | Porter | 141/102 X |
| 3,932,065 | 1/1976 | Ginsberg et al. | 251/7 X |
| 4,170,861 | 10/1979 | Snyder et al. | 53/381 A |

Primary Examiner—Horace M. Culver
Attorney, Agent, or Firm—Oliver D. Olson

[57] ABSTRACT

Spaced apart and covered Petri dishes are moved continuously toward a pair of spaced feed nozzles while the covers engage a ramp and are tilted upward away from the dishes to provide a space for reception of the feed nozzles. A photoelectric cell detects the passage of the dishes beneath the feed nozzles and controls the feeding of bacterial culture growth medium alternately from the nozzles into the dishes as the latter move continuously past the nozzles. The covers are replaced over the dishes after filling.

7 Claims, 13 Drawing Figures

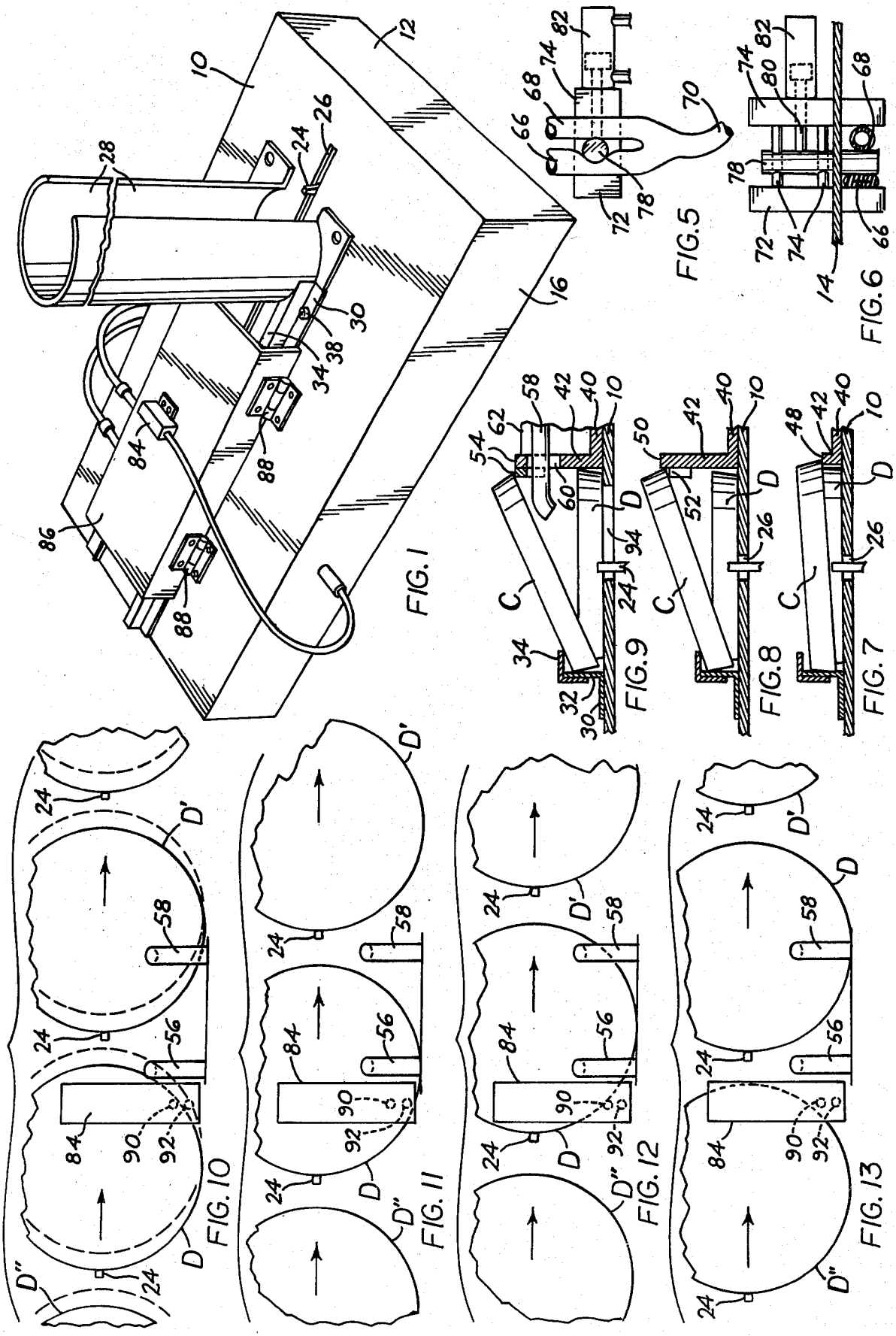

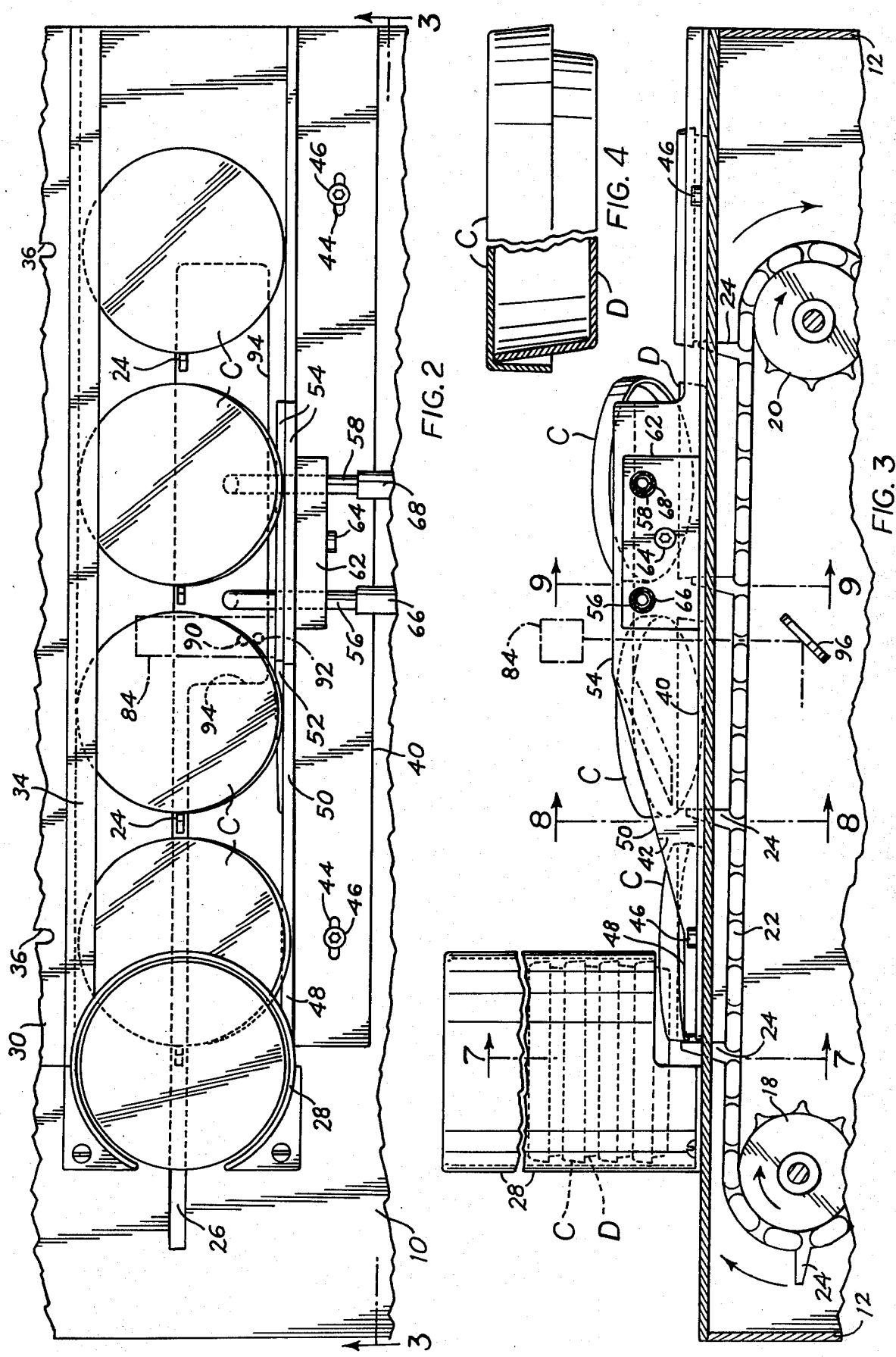

APPARATUS FOR FILLING PETRI DISHES

BACKGROUND OF THE INVENTION

Petri dishes, filled with agar-agar or other culture growth medium, are employed in vast numbers in many types of testing and research laboratories, and various types of apparatus have been proposed heretofore for the mass production of such filled dishes. In general, the rate of feed of growth medium in such apparatus must be restricted in order to prevent spillage from the dishes, and therefore the prior apparatus require either the intermittent stopping of each dish while it is filled with medium, or the speed of movement of the dishes is restricted to allow proper filling. Typical of such apparatus are those described in U.S. Pat. Nos. 3,050,915; 3,513,621; 3,719,023; and 4,170,861. In both types of apparatus the rate of production of filled dishes is limited, resulting in correspondingly high production cost.

SUMMARY OF THE INVENTION

In its basic concept, the dish filling apparatus of this invention provides a pair of feed nozzles spaced apart in the direction of movement of spaced apart dishes and operated alternately such that the trailing nozzle first feeds culture growth medium or other fluid material into a dish while the leading nozzle is shut off during its registry with the space between adjacent dishes, and the leading nozzle then feeds the fluid material into the same dish while the trailing nozzle is shut off during its registry with the space between said dish and the next succeeding dish.

It is by virtue of the foregoing basic concept that the principal objective of this invention is achieved; namely, to overcome the aforementioned production limitations of prior filling apparatus.

Another object of this invention is to provide apparatus of the class described by which Petri dishes may be filled with culture growth medium at about twice the production rate of prior apparatus.

A further object of this invention is the provision of apparatus of the class described in which the feeding of medium is controlled by cooperative relationship between the positions of a Petri dish and a photoelectric cell.

The foregoing and other objects and advantages of this invention will appear from the following detailed description, taken in connection with the accompanying drawings of a preferred embodiment.

BRIEF DESCRIPTION OF THE DRAWINGS

FIG. 1 is a foreshortened perspective view of Petri dish filling apparatus embodying features of this invention.

FIG. 2 is a fragmentary plan view of the apparatus shown in FIG. 1, with the protective cover removed.

FIG. 3 is a fragmentary, foreshortened, longitudinal section taken on the line 3—3 in FIG. 2.

FIG. 4 is a foreshortened side elevation of a Petri dish, a portion being broken away to disclose structural details.

FIG. 5 is a fragmentary side elevation of a feed nozzle control component of the apparatus.

FIG. 6 is a fragmentary sectional view as viewed from the top in FIG. 5.

FIGS. 7, 8 and 9 are fragmentary sectional views taken on the lines 7—7, 8—8 and 9—9, respectively, in FIG. 3 and showing progressive stages of upward lifting of Petri dish covers during movement of the dishes through the filling stage.

FIGS. 10, 11, 12 and 13 are fragmentary plan views in schematic form illustrating the relationships between the pair of spaced feed nozzles and adjacent Petri dishes and photoelectric cell feed control, during continuous movement of spaced dishes through the filling cycle.

DESCRIPTION OF THE PREFERRED EMBODIMENT

Although the apparatus of this invention may be employed to fill various types of fluid materials into various forms of dishes, it is particularly suited to the filling of agar-agar or other bacterial culture growth base medium into Petri dishes. The following description of the apparatus refers to this latter use merely for the purpose of illustration.

The apparatus of this invention includes a hollow housing which forms a base support for the components of the apparatus. The housing includes the top panel 10 supported by downwardly extending end walls 12, a front wall 14, and a rear wall 16. The housing also has a bottom wall (not shown).

Within the housing there is supported a pair of longitudinally spaced rotary sprockets 18 and 20 mounted on shafts and supporting an endless conveyor chain 22. A plurality of drive lugs 24 are secured to and project outwardly from the conveyor chain at longitudinally spaced intervals. The lugs on the upper working stretch of the chain project upwardly through a longitudinal slot 26 in the top panel of the housing for engaging and moving Petri dishes in a manner described more fully hereinafter. An electric motor (not shown) is connected to the downstream, or leading sprocket 20 i.e. the sprocket leading in the direction of movement of the upper working stretch of the conveyor chain, for effecting continuous movement of the chain and drive lugs.

Secured to the top panel of the housing and overlying the slot 26 adjacent the trailing end of the conveyor chain is an upwardly elongated hollow hopper 28 dimensioned to freely confine a vertical stack of Petri dishes with covers. FIG. 4 illustrates such a conventional Petri dish D and cover C. Thus, the dish includes a bottom wall and an upwardly extending peripheral wall, while the cover includes a top wall and a downwardly extending peripheral wall. The cover is dimensioned to fit loosely over the dish and both the dish and cover are made of transparent material such as glass, or, preferably inexpensive and therefore expendable synthetic resin.

As illustrated, the upwardly elongated hopper 28 is open at the rearward side for convenient access to the interior for filling with Petri dish and cover assemblies.

It is to be noted that the feed hopper is positioned relative to the upstream end of the conveyor such that each lug 24 on the conveyor chain projects upward through the slot in the housing top panel at the trailing end of the chain and engages the rearward side of the bottom-most dish and cover of the stack in the hopper. Thus, as the conveyor chain continues its downstream movement the trailing lug pushes the bottom-most dish and cover from under the stack and moves it forwardly out of the hopper. When the bottom-most dish and cover clears the hopper, the stack within the hopper drops by gravity so that the next bottom-most dish and cover is ready for engagement by the next succeeding lug that appears through the slot at the trailing end of the conveyor.

Means is provided for guiding the dishes and covers in the downstream direction of movement of the conveyor, while simultaneously effecting upward tilting of the covers from one side of the associated dishes. For this purpose an elongated dish guide and cover retainer strip is secured to the housing cover panel a spaced distance rearwardly of and parallel to the conveyor slot 26. This guide and retainer strip preferably is formed with a rearwardly extending base flange 30 for mounting on the housing top panel, a vertical intermediate wall 32 extending upwardly from the forward edge of the base flange, and a top flange 34 extending from the upper end of the vertical wall horizontally forward toward the conveyor slot. The base flange preferably is provided with a plurality of slots 36 elongated in the direction perpendicular to the longitudinal dimension of the flange and arranged to freely receive securing screws 38 therethrough for threaded engagement in a tapped opening in the housing top panel. By this means the retainer strip may be adjusted toward and away from the conveyor slot.

On the side of the conveyor slot opposite the retainer strip is located an elongated dish guide and cover lifting strip. It also extends parallel to the conveyor slot and includes a forwardly extending base flange 40 and an upstanding vertical wall 42. The base flange is provided with a pair of longitudinally spaced and longitudinally elongated slots 44 each arranged to freely receive a securing screw 46 therethrough for threaded engagement in tapped openings in the housing top panel. It is by this means that this dish guide and cover lifting strip is adjustable in the longitudinal direction, rather than the transverse direction of adjustment of the dish guide and cover retainer strip described hereinbefore.

The vertical walls 32 and 42 of the dish guide strips function to confine freely between them Petri dishes being moved by the conveyor in the downstream direction. Lateral adjustment of the retainer strip by the transverse slots 36 facilitates proper dimensioning of the space between the walls 32 and 42 for free movement of the dishes.

Associated with the vertical wall 42 is a contoured ramp configured for engagement of the adjacent portion of the underside of the side wall of covers C and raise them upwardly from their underlying dishes D, to create a space between the dishes and covers. At the upstream end adjacent the hopper the ramp is formed by the top edge 48 of the vertical wall 42. An adjacent portion 50 of this top edge then is angled upwardly in the downstream direction so as to initiate upward tilting of the cover.

During upward tilting of the cover by the ramp, the diametrically opposite portion of each cover is retained under the upper flange 34 of the retainer strip, so as to prevent disengagement of the cover from the associated dish. Accordingly, the drive lug 24 which initially abutted the rearward side of the cover as it engaged the bottom-most assembly in the hopper, now abuts the dish since the cover has been tilted upward out of engagement with the lug (FIG. 8). Since the top flange 34 of the retainer strip prevents disengagement of the cover from the associated dish, the cover is moved in the downstream direction with its associated dish as the latter is driven by the engaging conveyor lug.

As the ramp tilts the cover further upward, the peripheral wall of the cover is moved away from the top edge of the vertical wall 42 of the guide strip. Accordingly, the ramp is continued in the downstream direction by an inwardly projecting side extension of the vertical wall. This extension may be formed as a separate plate secured to the inner side of the vertical wall, or may be formed as an integral part of the vertical wall, as desired. This portion of the ramp is formed of the upwardly inclined portion 52 and the terminal, horizontal portion 54.

The purpose of raising the cover from each dish is to provide a space between them sufficient to receive a pair of longitudinally spaced feed nozzles 56 and 58 for introducing agar-agar or other desired culture growth medium into the dish. The paid of feed nozzles extend through openings 60 in the vertical wall 42 of the guide strip, in the area of greatest elevation of the cover by the ramp, i.e. under the ramp portion 54. The pair of nozzles are mounted in a support block 62 which is secured to the outer side of the vertical wall 42, as by means of a screw 64 threaded into a tapped opening in the vertical wall.

The longitudinally elongated slots 44 in the base flange 40 of the guide strip accommodates longitudinal adjustment of the latter and corresponding longitudinal adjustment of the cover lifting ramp and feed nozzles, for purposes described more fully hereinafter.

Means is provided for delivering culture growth medium alternately to each of the feed nozzles. In the embodiment illustrated, the outer ends of the feed nozzles are connected to one end of a pair of flexible hoses 66 and 68, the opposite ends of which merge into communication with a single flexible feed hose 70. The opposite end of the feed hose is connected to the outlet of a pump (not shown) the inlet of which communicates with a supply of agar-agar or other bacterial culture growth base material which is solid at room temperature but liquid at supply temperature. Although a variety of types of pumps may be utilized, a conventional peristaltic pump has been found to be quite suitable.

The pair of flexible hoses extend from the outer ends of the feed nozzles downward along the outer side of the front wall of the housing and between a pair of support plates 72 and 74 which extend outwardly through the front wall 14 of the housing. The portions of the support plates inwardly of the front wall mount a pair of guide bars 76 between them which slidably mount an elongated pinch bar 78. The pinch bar extends outwardly through an opening in the front wall of the housing, between the longitudinally spaced support plates.

The portion of the pinch bar inwardly of the front wall is secured to the projecting piston rod 80 of a fluid pressure cylinder 82, preferably an air cylinder, mounted on one of the support plates. Thus, by the application of fluid pressure selectively to the opposite ends of the cylinder, the pinch bar is moved toward one or the other of the spaced support plates. The flexible hoses leading from the feed nozzles are positioned on opposite sides of the pinch bar and between the support plates, and therefore movement of the pinch bar selectively toward one or the other of the support plates functions in the manner of a pinch clamp to pinch closed one of the flexible hoses while opening the other hose. In this manner, culture growth medium is delivered alternately to the pair of feed nozzles. The air cylinder drive for the pinch bar may be replaced with an electric solenoid, or other drive mechanism, as desired.

Means is provided for controlling the movement of the pinch bar in relation to the movement of spaced Petri dishes in the downstream direction past the pair of feed nozzles. In the embodiment illustrated, a photoelectric cell 84 is mounted on a transparent protective cover 86 which retractably overlies the guide strips downstream from the hopper. As illustrated, the protective cover is secured to the top panel of the housing by means of hinges 88, so that the cover may be retracted to expose the underlying components of the apparatus.

The photoelectric cell includes a light source 90 and a reflected light detector 92, and is positioned on the cover so as to provide the mode of operation illustrated in FIGS. 10-13 and described hereinafter. For this purpose the detector is arranged in the electric circuit of a solenoid valve in the air supply to the air cylinder 82. The arrangement is such that when the detector receives light reflected from the light source, it activates the solenoid valve to move the pinch bar toward the right in FIGS. 5 and 6 to close the right hand flexible hose 68 and open the left hand flexible hose 66 and thus allow delivery of growth medium to the left hand, or upstream feed nozzle 56. Similarly, when the detector receives no light reflection from the light source, it activates the solenoid valve to effect movement of the pinch bar toward the left in FIGS. 5 and 6 to close the left hand flexible hose 66 and open the right hand hose 68. Growth medium thus is delivered to the right hand, or downstream feed nozzle 58.

In FIG. 10 the Petri dish has been moved by the associated conveyor lug 24 to the position in which the light source 90 of the photoelectric cell impinges on the bottom of the dish and thus is reflected back to the detector 92. In the manner described hereinbefore, this effects movement of the pinch bar 78 toward the right in FIG. 5 to initiate delivery of bacterial culture growth medium to the left hand, or upstream feed nozzle 56. Since the Petri dish is moved continuously by the conveyor, it has moved toward the right to the broken line position illustrated in FIG. 10 before the medium is ejected from the nozzle into the dish.

Simultaneously with the movement of the pinch bar toward the right in FIG. 5, the delivery of growth medium to the next preceeding Petri dish D' has been stopped, by the time the Petri dish D has moved to the broken line position illustrated.

FIG. 11 illustrates the importance of preventing delivery of growth medium from the right hand, or downstream nozzle 58 while the latter registers with the space between the adjacent Petri dishes, as the latter are conveyed toward the right.

When the Petri dish D reaches the position illustrated in FIG. 12, the light source 90 of the photoelectric cell no longer reflects from the bottom of the dish. Instead, the light source is projected through an opening 94 in the housing top panel and into the interior of the housing, where it is deflected by an angularly disposed mirror 96 or other deflection surface so as to prevent it from reflecting back to the detector 92. Accordingly, the pinch bar is moved toward the left in FIG. 5 to close the left hand hose 66 and open the right hand hose 68. Delivery of growth medium to the left hand feed nozzle 56 is stopped, but is simultaneously initiated to the right hand feed nozzle 58. Thus, growth medium continues to be filled into the Petri dish D by the right hand feed nozzle while the left hand feed nozzle is in registry with the space between the Petri dish D and the next succeeding dish D".

The foregoing cycle of operation is repeated continuously to effect the filling of each Petri dish as it moves continuously toward the right. Since each dish receives a supply of growth medium from each of the pair of feed nozzles, first from the left hand or upstream feed nozzle 56 and then from the right hand or downstream feed nozzle 58, the speed of movement of the dishes by the conveyor may be substantially greater than possible heretofore. Indeed, it has been determined that the rate of production of filled Petri dishes is about twice the rate of production achieved by apparatus of the prior art.

After each Petri dish has been filled to the desired level with growth medium, its continued movement toward the right (FIGS. 2 and 3) carries the associated cover C with it beyond the terminal end of the cover-elevating ramp portion 54. The cover then falls by gravity back onto the associated Petri dish.

Referring primarily to FIG. 3 of the drawings, it is to be noted that the conveyor is mounted in the housing to provide a slight downward inclination of the conveyor chain in the downstream direction of movement thereof, so that the downstream lug 24 disengages from the Petri dish as the lug begins to move clockwise around the downstream sprocket. This arrangement prevents the downstream lug from flinging the filled and covered Petri dish violently forward as the associated lug acelerates in speed as it moves around the sprocket. The disengaged covered Petri dish is moved further forward by the next succeeding covered and filled dish. An offbearing conveyor (not shown) receives these filled and covered dishes and delivers them to refrigeration equipment where the growth medium is cooled to room temperature and thus is solidified in preparation for packaging for transport or storage.

It will be apparent to those skilled in the art that various changes may be made in the size, shape, type, number and arrangement of parts described hereinbefore, without departing from the spirit of this invention and the scope of the appended claims.

Having now described my invention and the manner in which it may be used, I claim:

1. Apparatus for filling Petri and like dishes with a fluid material, comprising:
   (a) conveyor means for moving a succession of dishes continuously in a downstream direction,
   (b) a pair of feed nozzles spaced apart in the direction of conveyor movement and arranged for registry with dishes as the latter are moved by the conveyor means,
   (c) conduit means communicating the nozzles with a supply of fluid material to be fed, and
   (d) feed control means in the conduit means operable to effect feeding of fluid material to each dish alternately first through the upstream nozzle as it registers with the continuously moving dish and second through the downstream nozzle as it registers with the continuously moving dish.

2. The apparatus of claim 1 wherein the feed control means includes electrically actuated drive means, and a photoelectric cell arranged to detect the presence and absence of a dish in proximity to the feed nozzles and to actuate the drive means to effect said alternate feeding of fluid material to the dish.

3. The apparatus of claim 2 wherein the photoelectric cell is arranged to direct a light toward a dish and to detect reflection of the light from the dish.

4. Apparatus for filling Petri and like dishes with a fluid material, comprising:
 (a) conveyor means for moving a succession of dishes continuously in a downstream direction,
 (b) a pair of feed nozzles spaced apart in the direction of conveyor movement and arranged for registry with dishes as the latter are moved by the conveyor means,
 (c) a pair of flexible hoses communicating the nozzles with a supply of fluid material to be fed, and
 (d) pinch clamp means arranged to retractably pinch closed the pair of hoses on an alternate cycle to effect feeding of fluid material to each dish alternately first through the upstream nozzle and second through the downstream nozzle as the dish is moved continuously past the nozzles.

5. The apparatus of claim 4 wherein the pinch clamp means includes a pinch bar, an electrically actuated drive means therefor and a photoelectric cell arranged to detect the presence and absence of a dish in proximity to the feed nozzles and to actuate the drive means to effect said alternate feed of fluid material to the dish.

6. The apparatus of claim 5 wherein the photoelectric cell is arranged to direct a light toward a dish and to detect reflection of the light from the dish.

7. Apparatus for filling Petri and like dishes with a fluid material wherein each dish is provided with a removable cover, the apparatus comprising:
 (a) conveyor means for moving a succession of dishes continuously in a downstream direction,
 (b) a pair of feed nozzles spaced apart in the direction of conveyor movement and arranged for registry with dishes as the latter are moved by the conveyor means,
 (c) conduit means communicating the nozzles with a supply of fluid material to be fed,
 (d) feed control means in the conduit means operable to effect feeding of fluid material to each dish alternately first through the upstream nozzle and second through the downstream nozzle as the dish is moved continuously past the nozzles,
 (e) a cover tilting ramp extending parallel to the conveyor means adjacent the feed nozzles and arranged to engage the side of a cover adjacent the feed nozzles and tilt it angularly upward from its dish sufficiently to allow the feed nozzles to enter the space between the dish and cover, and
 (f) a cover retainer member spaced from and extending parallel from the ramp on the opposite side of the conveyor and arranged to freely overlie the side of a cover opposite the ramp for retaining said side of the cover in engagement with its dish while the opposite side of the cover is tilted angularly upward from the dish.

* * * * *